US005674697A

United States Patent [19]
Carlson

[11] Patent Number: 5,674,697
[45] Date of Patent: Oct. 7, 1997

[54] HIGH SENSITIVITY IMMUNOASSAY FOR POLYCHLORINATED DIBENZO-P-DIOXINS AND POLYCHLORINATED DIBENZOFURANS

[75] Inventor: Robert E. Carlson, Minnetonka, Minn.

[73] Assignee: Ecochem Research, Inc., Chaska, Minn.

[21] Appl. No.: 404,969

[22] Filed: Mar. 16, 1995

[51] Int. Cl.$^6$ .................. G01N 33/535; G01N 33/547
[52] U.S. Cl. ............................. 435/7.93; 436/815
[58] Field of Search ......................... 435/7.93; 436/815

[56] References Cited

U.S. PATENT DOCUMENTS

| | | | |
|---|---|---|---|
| 4,238,472 | 12/1980 | Albro et al. | 424/12 |
| 4,798,807 | 1/1989 | Vanderlaan et al. | |
| 5,273,909 | 12/1993 | Piasio | 436/518 |
| 5,384,262 | 1/1995 | Latt et al. | 436/518 |
| 5,464,746 | 11/1995 | Fino | 435/7.8 |

FOREIGN PATENT DOCUMENTS

| | | |
|---|---|---|
| 242589 | 10/1987 | European Pat. Off. |
| 0251 635 | 1/1988 | European Pat. Off. |
| 0 258 006 A2 | 3/1988 | European Pat. Off. |
| 251635 A | 9/1993 | European Pat. Off. |
| 258006 A | 9/1993 | European Pat. Off. |
| 332819 A | 1/1994 | European Pat. Off. |
| WO 8809798 | 12/1988 | WIPO |
| 94/12536 | 6/1994 | WIPO |
| WO 9506249 A | 4/1995 | WIPO |

OTHER PUBLICATIONS

Christoffer Rappe and Hans Rudof Buser, "Chemical Properties and Analytical Methods", Himbrough (ed.) Halogenated biphenyls, terphenyls, napththalenes, dibenzodioxins and related products, Chpt. 2, 1980, pp. 40–76.

R.E. Carlson, "Hapten vs. Competitor Design Strategies for Immunoassay Development" in Judd O. Nelson, Alexander E. Karu, Rosie B. Wong, Eds., Immunoanalysis of Agrochemicals, ACS Symposium Series No. 586, Chpt. 10, 1995, pp. 140–152.

B.K. Van Weemen and A.H.W.M. Schuurs, "Sensitivity and Specificity of Hapten Enzyme–Immunoassays", in Feldman et al., Eds., First International Symposium on Immunoenzymatic Techniques, 1976, pp. 125–133.

Sherry et al., "Use of Dimethyl Sulfoxide as Solubilization Agent in the Detection of 2,3,7,8-TCDD by Radioimmunoassay", Chemosphere 20(10–12):1409–1416 (1990).

Kerkhoven et al., "The use of recombinant–DNA techniques and hybridomas to make antibody(–fragments) that specifically recognize well defined dioxins and dibenzofurans in a competitive ELISA", Dioxix '93, vol. 11:127–130 (1993).

Langley et al., "Immunoprobes for Polychlorinated Dibenzodioxins: synthesis of Immunogen and Characterization of Antibodies", Food & Agric. Immunol. 4:143–151 (1992).

Bunce et al., "Development of a Rapid Screening Assay for PCDDs and PCDFs", Chemosphere 20(10–12):1417–1422 (1990).

Collier, Thomas Lee, "Synthesis of dioxins as analytical and toxicological standards", Dissertation Abstracts International vol. 51, No. 12 (Jun. 1991), p. 5870B.

Dougherty et al., "High Affinity Assay for Polychlorodibenzodioxins and Polychlorodibenzofurans: Application to Hazardous Wastes", Abstract of a presentation to the meeting of the Division of Environmental Chemistry of the Amer. Chem. Soc. (Apr. 1986).

Watkins et al., "An Immunoassay for Chlorinated Dioxins in Soils", Chemosphere 19(1–6):267–270 (1989).

Sherry et al., "The Use of Radioimmunoassay for the Detection of Polychlorinated Dibenzo–P–dioxins in Fish Samples", Chemosphere 19(1–6):255–261 (1989).

Krieger, James, "Immunoassay for organic analyses developed", Chemical and Engineering News (Mar. 30, 1987), p. 22.

Stanker et al., "Development of an Immunoassay for Chlorinated Dioxins Based on a Monoclonal Antibody and an Enzyme Linked Immunosorbent Assay (ELISA)", Chemosphere 16(8/9):1635–1639 (1987).

Stanker et al., "Monoclonal Antibodies for Dioxin: Antibody Characterization and Assay Development", Toxicology 45:229–243 (1987).

Kennel et al., "Monoclonal Antibodies to Chlorinated Dibenzo–p–Dioxins", Chemosphere 15(9–12):2007–2010 (1986).

Kennel et al., "Monoclona Antibodies to Chlorinated Dibenzo–p–Dioxins", Toxicol. and Applied Pharmacol. 82:256–263 (1986).

Chae, et al., "A Screening Assay for the Tetrachlorodibenzo–p–dioxin Receptor using the [$^{125}$I]iodovaleramide Derivative of Trichlorodibenzo–p–dioxin as the Binding Ligand", Intern. J. Environ. Anal. Chem. 17:267–274 (1984).

Albro et al., "[47] Radioimmunoassays of Chlorinated Dibenzo–p–dioxins", Methods in Enzymology 84:619–628 (1982).

(List continued on next page.)

Primary Examiner—Mary E. Ceperley
Attorney, Agent, or Firm—Merchant, Gould, Smith, Edell, Welter & Schmidt, P.A.

[57] ABSTRACT

The present invention provides a method for determining qualitatively or quantitatively the presence of polychlorinated dibenzodioxins and polychlorinated dibenzofurans in a test sample. The method includes the steps of: providing a known quantity of antibodies to the polychlorinated dibenzodioxins and polychlorinated dibenzofurans; providing a competitor that will bind to said antibodies in competition with the polychlorinated dibenzodioxins and polychlorinated dibenzofurans and having a lower affinity to said antibodies than said antibodies have to the polychlorinated dibenzodioxins and polychlorinated dibenzofurans; incubating said antibodies and said competitor in the presence of a test sample; and detecting the presence of the polychlorinated dibenzodioxins and polychlorinated dibenzofurans in the test sample. The invention also provides methods of using the competitor of the present invention to detect qualitatively or quantitatively polycyclic aromatic compounds.

23 Claims, 4 Drawing Sheets

OTHER PUBLICATIONS

Luster et al., "Radioimmunoassay for Quantitation of 2,3,7,8–Tetrachlorodibenzofuran", Anal. Chem. 52:1497–1500 (1980).

Albro et al., "A Radioimmunoassay for Chlorinated Dibenzo–p–Dioxins", Toxicol. and Applied Pharmacol. 50:137–146 (1979).

"Paracelsian, Inc. (NASDAQ:PRLN) Announces Licensing Agreement for New Analytical Approach to Assessing Dioxin With Dow Environmental", Paracelsian release dated Jan. 17, 1995.

Robert O. Harrison, Maryanne Chamerlik–Cooper, Robert E. Carlson, "Determination of PCBs in Water, Soil, Sediment, and Oil by Enzyme Immunoassay", Proceedings: 1991 EPRI PCB Seminar, Oct. 8–11, 1991, Baltimore, Maryland.

Robert O. Harrison, Robert E. Carlson, "Analysis of PCBs by Enzyme Immunoassay", 8th Annual Waste Testing and Quality Assurance Symposium, Jul. 1992, Arlington, Virginia. Transcript of presentation.

Robert O. Harrison, Robert E. Carlson, Alan J. Weiss, "Analysis of PCBs by Enzyme Immunoassay", Third International Symposium on Field Screening, Las Vegas, Nevada, Feb. 1993.

Boehringer Manheim, Opposition to European Patent 0332819, Aug. 8, 1994.

J. McKinney, et al., "Development and Reliability of a Radio Immunoassay for 2,3,7,8–tetrachlorodibenzo–P–dioxin", Chemical Abstracts 96:209 (1982).

Vanderlaan, et al., "Improvement and Application of an Immunoassay for Screening Environmental Samples for Diosin Contamination", Env. Toxicol. 7:859–870 (1988).

R. O. Harrison, et al., "On–Site Analysis of PCB's in Water by Enzyme Immunoassay", Presentation prepared for the ACS National Meeting Mar. 1994, San Diego, CA.

Menzie et al., "Exposure to Carcinogenic PAHs in the Environment", Environ. Sci. Technol. 26(7):1278–1284 (1992).

L. Smith et al., Anal. Chem., vol. 50, No. 11, pp. 1830–1841 (1984).

HIGH SENSITIVITY IMMUNOASSAY FOR POLYCHLORINATED DIBENZO-P-DIOXINS AND POLYCHLORINATED DIBENZOFURANS

TECHNICAL FIELD

This invention relates to a sensitive method for detecting the presence or amount of polychlorinated dibenzo-p-dioxins and polychlorinated dibenzofurans in a test sample by immunoassay, and to hapten and competitor reagents for use in such an analysis.

BACKGROUND OF THE INVENTION

Polychlorinated Dibenzo-p-Dioxins and Polychlorinated Dibenzofurans—General

Polychlorinated dibenzo-p-dioxins (PCDDs) and polychlorinated dibenzofurans (PCDFs) are significant environmental pollutants that generally require complex and expensive methods for their analysis. R. E. Clement, *Anal. Chem.*, 63, 1130A (1991). PCDDs and PCDFs include chemically and physically stable mono- to octachloro derivatives of dibenzo-p-dioxin and dibenzofuran which are, typically, produced as by-products of various chlorination and combustion processes. Thus, what is referred to as polychloro dibenzodioxin or polychloro dibenzofuran, PCDD or PCDF, is a class of discrete chemical compounds, called congeners, having the general formulas $C_{12}H_xCl_yO_2$ and $C_{12}H_xCl_yO$, where x=0–7 and y=8–x.

PCDO    m+n=1–8

PCDF

The chemical and physical stability of PCDD and PCDF is a primary reason PCDD and PCDF pose such a significant environmental contamination problem. Because PCDDs and PCDFs do not readily degrade in the environment after disposal or dissemination, and are lipophilic, they are persistent and tend to accumulate in living organisms. PCDDs and PCDFs have been shown to be widespread environmental pollutants, occurring in most human and animal adipose samples, milk, sediment and numerous other matrices.

Animal studies with both mixtures and individual congeners of PCDD or PCDF have shown a variety of acute and chronic toxic effects. G. Mason, et al., *Toxicology*, 41, 21 (1986). At the present time, a dioxin congener, 2,3,7,8-tetrachlorodibenzo-p-dioxin, is believed to be the most acutely toxic environmental contaminant known. The significance of the PCDDs and PCDFs is currently one of the most studied aspects of environmental toxicology. Anon, *Environ. Sci. Technol.*, 29, 26A–28A (1995). Hence, there is wide interest in improved methods for detecting and measuring levels of all PCDDs and PCDFs in biological and environmental samples. Since the different congeners vary in toxicity, it is useful to detect individual congeners or the toxic congeners as well.

Several EPA rules governing PCDDs/PCDFs are of concern to analytical chemists, industry, and government as they require determination of PCDDs or PCDFs in various matrices. Most significantly, while EPA regulations typically require the determination of hazardous contaminants at the part-per-billion level, PCDDs and PCDFs must frequently be determined at the part-per-trillion or even the part-per-quintillion level. Restrictions on materials which are contaminated with even low levels of PCDD or PCDF has made proper evaluation of contamination by PCDD or PCDF a significant concern.

While regulation of PCDD and PCDF differs from country to country, there is a common analytical interest in determining the presence and amount of PCDD or PCDF and of their toxic congeners in the environment, and in materials that are potential sources of PCDD or PCDF to the environment. Regardless of the laws and rules, the analytical needs are similar: reliable, practical, and high sensitivity methods that can determine PCDD or PCDF and their toxic congeners in a variety of matrices.

The widespread occurrence of PCDD and PCDF in the environment requires a comprehensive assessment of their environmental impact. This assessment is particularly difficult because some congeners are more toxic than others. The difference in toxicity from the most toxic known congener to the least toxic known PCDD or PCDF is more than a factor of one million. The analysis of a sample of PCDD or PCDF is particularly complicated because PCDDs are a mixture of 75 congeners and the PCDFs are a mixture of 135 congeners.

This broad range in toxicity of PCDDs and PCDFs and the numerous toxic congeners of these species complicates the analysis of a test sample. Not only is it necessary to analyze for total PCDD or PCDF. It is clear that specific, high sensitivity analysis of the toxic PCDD or PCDF congeners in the environment is required for an objective evaluation of risk and environmental impact. However, the time, effort and expense associated with the congener specific analysis of these compounds by instrumental methods such as capillary gas chromatography, which can cost up to $2,000- per sample, places substantial constraints on the scope of risk assessment and site evaluation studies.

Polychlorinated Dibenzo-p-dioxins and Polychlorinated Dibenzofurans—Analysis

The present methods for the congener specific analysis of PCDD or PCDF typically use high-resolution gas chromatography with ion capture or mass spectrometer detection systems. R. E. Clement, *Anal. Chem.*, 63, 1130A (1991). Although these methods are relatively accurate, they are also very expensive and time consuming because of their reliance on sophisticated analytical instrumentation and skilled operators. Immunoassay based analytical methods have demonstrated value for specific, high throughput screening as well as quantititative analyses of many environmental analytes. J. P. Sherry, *Crit. Reviews Anal. Chem.*, 64, 217–300 (1992). Moreover, immunoassay can be accomplished with minimal sample preparation and instrumentation.

Existing immunoassays for PCDD or PCDF are radioimmunoassays (RIAs) and enzyme immunoassays (EIAs) that give varying specificity for the PCDD and PCDF. More importantly, the highest sensitivity achieved for the toxic congeners is typically no better than ca. 1 ng per assay well, tube, etc. As a result of this low sensitivity, toxic levels of PCDD or PCDF can elude detection by these assays.

Accordingly, there is a need for a sensitive immunoassay that can detect PCDD or PCDF. There is a need for an immunoassay that can detect PCDD or PCDF at the low levels that can cause toxic effects. In addition, it is advantageous to detect the toxic congeners of PCDD and PCDF in an immunoassay. Such immunoassays can offer significant advantages in cost, personnel training, and equipment requirements over present immunoassays and provide substantially improved sensitivity over the known methods.

SUMMARY OF THE INVENTION

The present invention provides a method of determining the presence or amount of PCDD of PCDF in a test sample. That is, the present invention provides both qualitative and quantitative analysis methods for PCDD or PCDF. The methods of the present invention are immunoassays that preferably utilize a competitor reagent to accurately detect the presence and the amount of PCDD or PCDF in a test sample, at greater sensitivity than currently used immunoassays. The competitors of the present invention compete with the PCDD or PCDF present in a test sample for binding sites on antibodies that recognize and bind to the PCDD or PCDF. Antibodies are raised by conjugating a hapten of the present invention with a protein carrier and injecting the conjugate into an animal. Competitors and haptens of the present invention can be used in a number of assay formats to detect PCDD or PCDF with greater sensitivity than existing methods.

An assay method of the present invention comprises the steps of: a) providing a known quantity of antibodies to PCDD or PCDF; b) providing a competitor that will bind to said antibodies in competition with PCDD or PCDF; c) incubating said antibodies and said competitor in the presence of a test sample; and d) detecting the presence of PCDD or PCDF in the test sample.

Preferably, to improve sensitivity said competitor will have lower affinity to said antibodies than said antibodies have to the PCDD or PCDF. Also, the step of incubating the antibodies and competitor in the presence of a test sample is preferably carried out for a period of time sufficient to obtain a reproducible relationship between the quantity of competitor bound to the antibodies and the quantity of PCDD or PCDF in the test sample. Preferably, the step of detecting the presence of PCDD or PCDF involves measuring the amount of PCDD or PCDF in the test sample, i.e., carrying out a quantitative analysis. This can occur using a labeled competitor and by measuring the amount of antibody bound to said labeled competitor. In certain embodiments, however, the detecting step involves measuring the amount of unbound competitor in the test sample.

"Test sample", as used herein, refers to a sample to be tested for the presence of PCDD or PCDF. The test sample may be in liquid or solid form, and will include solid samples, oil samples, tissue samples and other samples potentially containing PCDD or PCDF.

"Polycyclic heteroatomic aryl compound", as used herein, refers to polychloro dibenzodioxins or polychloro dibenzofurans, which include classes of chemical compounds having the general formulas $C_{12}H_xCl_yO_2$ and $C_{12}H_xCl_yO$, where $x = 0-7$ and $y = 8-x$.

PCCD    m + n = 1–8

PCDF

A "hapten" is a molecule that when combined with a carrier protein induces an immune response in an animal. For purposes of this invention, the hapten is designed to raise antibodies that recognize and bind to PCDD or PCDF. The competitor reagents of the present invention are designed to improve the sensitivity of the assay format selected. The competitor will bind to the antibodies raised from hapten-protein complexes of the invention in competition with PCDD or PCDF in a test sample.

The present invention provides novel competitors described by the following general formula(s):

FORMULA I

FORMULA II

FORMULA III

FORMULA IV

FORMULA V

FORMULA VI

FORMULA VII wherein
- (a) A is a single bond or an organic or inorganic linking group capable of forming covalent bonds with a phenyl ring and with B simultaneously.
- (b) B is a single bond or an organic or inorganic linking group capable of forming covalent bonds with A and C simultaneously;
- (c) C is a single bond or an organic or inorganic linking group capable of forming simultaneous covalent bonds with B and a conjugate moiety;
- (d) D is a single bond or an organic or inorganic linking group capable of forming covalent bonds with an alkyl ring and with E;
- (e) E is a single bond or an organic or inorganic linking group capable of forming covalent bonds with D and F simultaneously;
- (f) F is a single bond or an organic or inorganic linking group capable of simultaneously forming covalent bonds with E and a conjugate moiety;
- (g) l=0–5;
- (h) m=0–4;
- (i) n=0–3;

Competitors of Formula I are preferred as they are expected to provide, in general, greater sensitivity than the competitors of Formula II–VII. Competitors of Formula I are expected to bind anti-hapten antibodies with a lower affinity than the affinity with which the PCDD or PCDF will bind to the anti-hapten antibodies. A conjugate moiety can be a protein, a solid support, a label, and the like, to which a skilled worker would bond a competitor or hapten to form a conjugate.

Preferably the methods, competitors, haptens and other components of the invention detect or are directed toward detecting the more toxic congeners of PCDD or PDCF, most preferably the most toxic congeners of PCDD or PCDF.

Haptens from which antibodies for use in the present immunoassay can be raised include those described by Formula VIII and IX:

FORMULA VIII

FORMULA IX wherein
- (a) L is a single bond or an organic or inorganic linking group capable of forming covalent bonds with a phenyl ring and with M simultaneously;
- (b) M is a single bond or an organic or inorganic linking group capable of forming covalent bonds with A and C simultaneously;
- (c) N is a single bond or an organic or inorganic linking group capable of simultaneously forming covalent bonds with M and a conjugate moiety;
- (d) m=0–4;
- (e) n=0–3;

Polycyclic heteroatomic aryl compounds, defined herein, are members of a larger class of compounds. That larger class of compounds is referred to herein as "fused polycyclic compounds". Fused polycyclic compounds include compounds with at least 2 fused rings, including heterocyclic rings, at least one of which is aromatic. Fused polycyclic compounds include compounds such as polycyclic aromatic hydrocarbons which are defined in copending application "Immunoassay for Polycyclic Aromatic Compounds" which was filed on even date herewith. Fused polycyclic compounds also include polycyclic heteroatomic aryl compounds, naphthalene, indene, fluorene, indacene, anthracene, pyrene, naphthacene, chrysene, picene, ovalene, indole, quinolines, quioxazoline, carbazole, acridine, phananthroline, polycholorinated terphenyls, diphenyl ethers, xanthones, xanthenes, dibenzodioxin, benzodioxin, benzofuran, dibenzofuran, these compounds with substituents appended, congeners of these compounds, isomers of these compounds, and the like. Suitable substituents that can be appended to these compounds include halogen, alkyl, aryl, alkylaryl, heteroaryl, hydroxyl, alkoxyl, amino, thiol, or thioether substituents, and the like. Preferred fused polycyclic compounds include polycyclic aromatic hydrocarbons, polycyclic heteroatomic aryl compounds, derivatives of these compounds, congeners of these compounds, isomers of these compounds, and the like.

Fused polycyclic compounds include compounds described by the general structures Formula X and Formula XI:

FORMULA X

FORMULA XI

In Formulas X and XI the aromatic rings shown can have 1 or more, preferably not more than 2, carbon atoms substituted as nitrogen, sulfur, or oxygen. More preferred compounds lack heteroatoms. The substituents P, Q, R, S, T, U, V, and W can, preferably, be linked to form ring systems, preferably aromatic ring systems including up to a maximum of about 9 aromatic rings. The substituents P, Q, R, S, T, U, V, and W can be selected independently from substituents such as aryl, alkyl, aryl alkyl, unsaturated alkyl, heteroaryl, heteroalkyl, heteroarylalkyl, halogen, hydrogen, hydroxyl, thiol, thioalkyl, amino, and the like. The compounds described by Formulas X and XI typically have molecular weights less than about 1000.

The competitors of Formula I can be used to detect qualitatively or quantitatively fused polycyclic compounds using an assay method comprising the steps of: a) providing a known quantity of antibodies to a fused polycyclic compound; b) providing a competitor that will bind to said antibodies in competition with the fused polycyclic compound; c) incubating the antibodies and the competitor in the presence of a test sample; and d) detecting the presence of the fused polycyclic compound in the test sample.

DETAILED DESCRIPTION OF THE INVENTION

BACKGROUND—IMMUNOASSAY

Immunoassays are based on antigen-antibody interactions. Antibodies are serum proteins, typically with two sites that enable binding to target molecules (antigens). The antibody combining site is a complex, folded surface. Binding is influenced by hydrophobic and ionic forces as well as geometric fit. The bulk of the antibody protein is not involved in the combining site and can provide a site for covalent attachment to marker molecules, such as enzymes, radionuclides, or fluorophores.

A hapten is a small molecule (e.g., less than ca. 1000 daltons) that does not induce an immune response by itself, but is recognized by some antibodies. An immune response is induced by injecting a complex of the hapten and a carrier (typically greater than ca. 4000 daltons), which is typically a protein, into an animal. The complex can result from a physical association of the protein and hapten, such as is obtained from the mixing of a lipophilic hapten (e.g., PCDD, PCDF) with permethylated BSA, or from a covalent interaction such that a protein-hapten conjugate is formed.

A wide range of antibodies are produced in response to immunization with a hapten-protein complex. Most of the antibodies will react with the protein alone or with some complex of the protein, hapten and linkage groups. Only a few of the antibodies produced will bind with high affinity to the hapten alone, i.e., with no contribution of the protein and/or linker to the binding site. These antibodies are the ones which are most desirable for immunoassays aimed at detecting hapten-like chemicals.

Both polyclonal and monoclonal antibodies are readily prepared and suitable for the immunoassay of the present invention. The antibodies raised from injection of a hapten-protein complex into an animal can be isolated by conventional, well-known antibody isolation techniques.

Immunoassays to environmental pollutants are described in copending applications entitled Immunoassay to Toxic Congeners of Polychlorinated Biphenyls, Immunoassay for Polycyclic Aromatic Hydrocarbons, which were filed on even date herewith, and application Ser. No. 08/259,046, Immunoassay for Polychlorinated Biphenyls, which are incorporated herein by reference.

Polychlorinated Dibenzo-p-Dioxins and Polychlorinated Dibenzofurans—Toxic Congeners The analysis of a sample containing PCDD or PCDF is complicated because the PCDDs are a mixture of 75 congeners and the PCDFs are a mixture of 135 congeners. Both the PCDD and PCDF congeners vary dramatically in their toxicity. The relationship of toxicity to congener structure is believed to be based on induction of cytochromes, mixed-function oxidases and other microsomal enzymes, immunotoxicity, and receptor binding. The most toxic PCDD/PCDF congeners are thought to have the highest binding affinity for the cytosolic aryl hydrocarbon receptor, which regulates aryl hydrocarbon hydroxylase. S. Bandiera, et al., *Chem. Biol. Interact.*, 39, 259–277 (1982). The degree of toxicity of aryl compounds can be expressed in terms of toxicity equivalency factors (TEFs). These factors measure the toxicity of a compound relative to the toxicity of a standard reference. The reference compound is 2,3,7,8-tetrachlorodibenzo-p-dioxin (2,3,7,8-TCDD), which has been characterized as the most toxic anthropogenic compound known. This compound is given a reference TEF value of 1.0. Thus, if a given compound is observed to have toxicity which is 1/100th that of 2,3,7,8-TCDD, it has a TEF of 0.01. That is, if 1 ng/gram body weight 2,3,7,8-TCDD will produce a given toxicological endpoint and the compound in question requires 100 ng/gram body weight to produce the same effect, its TEF=1 ng/gram body weight 2,3,7,8-TCDD/100 ng/gram test compound=0.01. U.S.E.P.A. Report No. EPA/625/3-89016 (1989). The observed toxicities of the PCDD and PCDF cover a very wide range of potencies. The less toxic congeners of PCDD or PCDF typically have TEFs less than about 0.00001. Toxic congeners of PCDD or PCDF typically have TEFs from about 0.00001 to about 1. The most toxic congeners of PCDD or PCDF have TEFs from about 0.001 to about 1. The most toxic congeners include [S. Safe, *Crit. Rev. Toxicol.*, 21, 51–88 (1990)]:

| Chlorine Substitution | TEF |
|---|---|
| Dibenzo-p-dioxins | |
| 2,3,7,8-tetrachloro | 1.0 |
| 1,2,3,7,8-pentachloro | 0.5 |
| 1,2,3,4,7,8-hexachloro | 0.1 |
| 1,2,3,6,7,8-hexachloro | 0.1 |
| 1,2,3,7,8,9-hexachloro | 0.1 |
| 1,2,3,4,6,7,8-heptachloro | 0.01 |
| 1,2,3,4,6,7,9-heptachloro | 0.01 |
| Octachloro | 0.001 |
| Dibenzofurans | |
| 2,3,7,8-tetrachloro | 0.1 |
| 1,2,3,7,8-pentachloro | 0.05 |
| 2,3,4,7,8-pentachloro | 0.5 |
| 1,2,3,4,7,8-hexachloro | 0.1 |
| 1,2,3,6,7,8-hexachloro | 0.1 |
| 1,2,3,7,8,9-hexachloro | 0.1 |
| 2,3,4,6,7,8-hexachloro | 0.1 |
| 1,2,3,4,6,7,8-heptachloro | 0.01 |
| 1,2,3,4,7,8,9-heptachloro | 0.01 |
| Octachloro | 0.001 |

The toxicity equivalency quotient (TEQ) is derived from the TEF of each identified contaminant and its observed concentration. For example, 1 ng/g body weight of 2,3,7,8-TCDD has a TEQ of 1 ng/g (1 ng/g×1.0 TEF) while a 100 ng/g body weight concentration of 1,2,3,4,6,7,8-heptachlorodibenzo-p-dioxin also has a TEQ of 1 ng/g (100 ng/g×0.01 TEF). The total aryl compound toxicity which results from the body burden of the aryl compound contaminants has been estimated for a number of species using the TEQ. In several studies, the toxic congeners of PCDD or PCDF have accounted for a substantial portion of the total TEQ.

Assay

Competitors and haptens of the present invention are useful in a number of assay formats. Once suitable antibody (antisera) has been raised using a hapten of the present invention (Formula VIII and IX), the antibodies and competitors of the invention (Formulas I–VII) are incorporated into a suitable immunoassay. Enzyme ImmunoAssay (EIA) is a preferred format because of significant advantages in cost, personnel training and equipment requirements over radioimmunoassay and fluoroimmunoassay.

Other than enzymes, radioisotopes, luminescent molecules, fluorescent molecules, chemiluminescent molecules, and other detectable moieties may be part of an assay designed to take advantage of improved sensitivity available from use of haptens and competitors set forth herein. These detectable moieties can be bound to the antibodies or competitors of the present invention. Of the preferred enzymatic methods for determination, one particularly preferred method involves an EIA technique.

One assay procedure that may be used for the analysis of samples containing PCDD or PCDF is one in which antibodies are immobilized on the walls of a plastic support (test tubes or plastic wells). This immobilization can be either direct or through an immobilized anti-mouse antibody, anti-rabbit antibody, or the like. In such an assay procedure the standards and test samples are mixed with a limited amount of competitor conjugated directly to an enzyme, such as alkaline phosphatase or horseradish peroxidase. The free compound (PCDD or PCDF analyte) in the sample competes with the enzyme conjugate for binding to the immobilized antibody. Enzyme substrate and chromogen are added for color development by the bound enzyme. The intensity of the color is inversely proportional to the amount of PCDD or PCDF content. See, e.g., A. Voller, "Heterogenous Enzyme Immunoassays and their Applications", *Enzyme Immunoassay*, CRC Press, p. 183 (1980).

An initial step in one preferred embodiment of the assay process is to immobilize an antibody on a solid support, such as a plastic surface (e.g., inside a plastic test tube or in the well of a microtiter plate). After the antibody is immobilized, the support is washed to remove the unbound material. Simple adsorption is generally sufficient for immobilization. Alternatively, the antibody can be immobilized by binding to an anti-antibody second antibody which has been immobilized on the solid support.

Subsequently, a sample containing the analyte (PCDD or PCDF) is added in solution either from a standard or as part of the sample being analyzed. The competitor enzyme conjugate is then added. When no PCDD or PCDF is in the solution, a maximum amount of competitor enzyme conjugate binds to the antibody on the plate. A high concentration of PCDD or PCDF in solution blocks binding of the competitor enzyme conjugate to the antibody bound to the plate. At intermediate concentrations of PCDD or PCDF, some competitor enzyme conjugate will be bound to the antibody and some will remain in solution. At the end of the incubation period, the solution phase is washed away, leaving behind that fraction of the competitor enzyme conjugate that is bound to the immobilized antibody. The competitors are preferably a competitor of Formula I–VII above, more preferably Formula I, and most preferably one of the exemplified competitors (1–12) below.

A subsequent step in the preferred assay is the detection of the competitor enzyme conjugate which remains bound to the antibody. This is done by detecting the enzymatic activity associated with the competitor enzyme conjugate. A wide variety of enzymes and substrates are suitable. Enzymatic activity is most often demonstrated by the release of a colored product that can be detected spectrophotometrically.

In addition to these EIA protocols, reagents of the present invention will be usable in the development of a variety of assay formats. Examples include fluorescence, chemiluminescence, and luminescence methods, dipsticks and other rapid test devices for semi-quantitative use, fluorescence sensors, electrodes, and other sensor devices. Also the reagents of the present invention, i.e., competitors and haptens, may be used in the methods described in European Patent Application Nos. EP 0 242 589 and EP 0 258 006 A2 and U.S. Pat. Nos. 4,238,472 and 4,798,807, which are incorporated herein by reference.

Haptens

Haptens are used to produce antibodies for use in the assays of the present invention. A suitable hapten is conjugated with a carrier protein and injected into an animal (e.g. mice, rabbits, goats, horses) to induce an immune response. Suitable carrier proteins include keyhole limpet hemocyanin (KLH), bovine serum albumin (BSA) egg ovalbumin, thyroglobulin, bovine gamma globulin, and others known in the art (e.g., U.S. Pat. No. 4,456,691, incorporated herein by reference). The haptens of the present invention may be complexed with, or conjugated to, a carrier protein using a variety of methods known to those skilled in the art.

Suitable haptens include those having the general Formula VIII and IX. Haptens of general Formula VIII can produce antibodies that recognize either PCDD or PCDF. Haptens of general Formula IX can produce antibodies that recognize either PCDD or PCDF. Preferred haptens include those haptens of Formula VIII and IX wherein L is —O—, —S—, —CH$_2$—, —CH=CH— or —C(O)—. Examples of suitable haptens include Exemplary Haptens I–XV (n=1–30):

The substituents in the general formulas for the haptens and competitors have been described in functional terms herein above. These substituents can be defined in structural terms as well. Substituent A or D in Formulas I–VII and substituent L in Formulas VIII and IX are preferably selected from the group consisting of —NH—, —S—, —O—, —CH$_2$—, —C(O)—, —CH=CH—, —NH—C(O)—, —C(O)—NH—, —NH—C(O)—NH—, —NH—C(S)—NH—, —N(CH$_3$)—, —N(CH$_3$)$_2$—, and —OC(S)NH—. Preferably these substituents are selected from the group consisting of —O—, —S—, —CH$_2$—, —C(O)— and —CH=CH—.

Substituent B or E (Formulas I–VII) and substituent M (Formulas VIII and IX) represent an alkyl group that is optionally interrupted by 1–10 O, S, or NH groups. That is, the alkyl group can be a straight or branched saturated carbon chain with 0–10 O, S, or NH groups within the chain. Preferably, if one or more of these groups are present they are not in sequence with each other. That is, each is bonded to two carbon atoms within the chain.

Substituent C or F in Formulas I–VII and substituent N in Formulas VIII and IX are preferably selected from the group consisting of —CO$_2$H, —NH$_2$, —CHO, and —OH. Substituent D in Formulas I–VII is preferably selected from the group consisting of —CH$_2$— and —CH=CH—.

In the context of the present invention with respect to the substituents in Formulas I–IX, the term "organic group" means an aromatic, heterocyclic, saturated or unsaturated linear, branched, or cyclic hydrocarbon group. This term is used to encompass alkyl or vinyl groups, for example. The term "heterocyclic" means a mono- or polynuclear saturated or unsaturated cyclic radical containing carbons and one or more heteroatoms such as nitrogen, oxygen, phosphorus, silicon, or sulfur or combination thereof in the ring or rings. The term "aromatic" group means a mono- or polynuclear aromatic hydrocarbon group, including arylalkyl groups. The term "arylalkyl" group means a linear, branched, or cyclic alkyl hydrocarbon radical having a mono- or polynuclear aromatic hydrocarbon or heterocyclic substituent.

The haptens of the present invention can also be immobilized on a solid support to form a hapten-solid support complex. Suitable solid supports include inorganic supports such as glass, quartz, ceramics, zeolites, etc., polymeric materials derived from monomeric units such as styrene, divinylbenzene, ethylene, butadiene, etc., carbohydrate supports such as agarose, dextrose, cellulose, starch, etc., and insoluble protein materials such as gelatin, collagen, etc.

Competitors

The sensitivity of immunoassays of the present invention are enhanced with the use of a suitable competitor to compete with the analyte (PCDD or PCDF) in the test sample for binding with the antibody. That is, sensitivity of the immunoassay may be enhanced by selecting a competitor that does not substantially duplicate the hapten. The competitor must only be sufficiently recognized by the antibody to perform its function of competitively (versus the analyte) binding to the antibody. For example, the use of a phenyl competitor (Formula I) is preferred over use of a multiple ring competitor (Formulas II–VII). Competitors with fewer rings are preferred over competitors with the same number of rings as the analyte. A preferred competitor is typically smaller than the analyte. Thus, competitors of Formula II, Formula III, Formula V, and Formula VI are preferred over competitors of Formula IV and Formula VII. In addition, compared to an analyte, a preferred competitor can have fewer favorable interactions with the antibodies perhaps due to fewer or different functional groups that interact with the antibody. The preferred competitor may have different hydrophobicity than the analyte. For example, the use of an alkyl linker (A–B–C, D–E–F) on the competitor versus a polar linker on the hapten, may produce improved sensitivity. To enhance sensitivity, the competitor is selected such that it has a lower affinity with the antibody than the antibody has with the PCDD or PCDF in a test sample. The relative affinity of a particular antibody or antisera for the analyte versus a particular competitor can be measured using, for example, equilibrium dialysis. The most common format for this evaluation would utilize a solution of the antibody to which was added a particular $^{14}$C-labeled congener (e.g., 2,3,7,8-tetrachlorodibenzo-p-dioxin) either alone or in competition with a competitor.

Competitors of the present invention have one of the general structures of Formulas I–VII above. Each of the competitors is suitable for use in immunoassays for PCDD or PCDF. In fact, a competitor more closely resembling PCDD than PCDF could result in higher sensitivity for PCDF. Conversely, a competitor more closely resembling PCDF than PCDD could provide higher sensitivity for PCDD. Preferred competitors include Exemplary Competitors 1–20 (n=1–30):

Of the competitors of Formula II–VII, the competitors based on the alkyl/alkene link (A–B–C or D–E–F in Competitors 13, 16, 19 and 20 below) when used with antibodies raised from haptens using a polar chlorine mimic linker (e.g. —NH—, —S—, —O—, etc.) may have the best sensitivity of the competitors. By polar chlorine mimic linker it is meant that the group which attaches the linker to the biphenyl nucleus has properties of size, electronegativity, etc. which resemble chlorine. For example, the ether (—O—) and thioether (—S—) groups are expected to be good chlorine mimic moieties while the alkyl (—CH$_2$—) group is expected to be a poorer chlorine mimic. Herein, a "linker" is represented by A–B–C in Formulas I, II, IV, V and VII, by D–E–F in Formulas III and VI and by L–M–N in Formulas VIII and IX.

The competitors of the present invention can be bound to proteins. Suitable proteins include keyhole limpet hemocyanin (KLH), bovine serum albumin (BSA) egg ovalbumin, thyroglobulin, bovine gamma globulin, and others known in the art (e.g., U.S. Pat. No. 4,456,691, incorporated herein by reference). The competitors of the present invention may be complexed with, or conjugated to, a carrier protein using a variety of methods known to those skilled in the art.

The competitor is preferably used in a labeled or immobilized format. That is, preferably the competitor is labeled with a detectable moiety, such as an enzyme, radioisotope, chemiluminescent molecule, fluorescent molecule, luminescent molecule, or other detectable moiety known in the art. The competitor can also be immobilized on a solid support to form a competitor-solid support complex. Suitable solid supports include inorganic supports such as glass, quartz, ceramics, zeolites, etc., polymeric materials derived from monomeric units such as styrene, divinylbenzene, ethylene, butadiene, etc., carbohydrate supports such as agarose, dextrose, cellulose, starch, etc., and insoluble protein materials such as gelatin, collagen, etc.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

Examples

General Experimental Procedures

All reagents were purchased from Aldrich Chemical Co. or Sigma Chemical Co. unless otherwise indicated. Thin layer chromatography (TLC) was performed on Analtech 250 µm silica gel GF Uniplates. Flash column chromatography was performed using hand packed 40 µm silica gel columns. NMR spectra were recorded with Nicolet NT-300 or IBM 0200 MHz instruments. Mass spectra were typically obtained with an AEI-ms 30 spectrometer.

Hapten Synthesis

The haptens (Exemplified Haptens I–XV) can be prepared using known synthetic strategies.

Competitor Synthesis

The competitors (Exemplified Competitors 1–20) are readily available from commercial sources or by the addition of a linker moiety to an appropriately functionalized phenyl, benzodioxin, benzofuran, dibenzodioxin or dibenzofuran synthon.

Antibody Preparation

Figure 1:
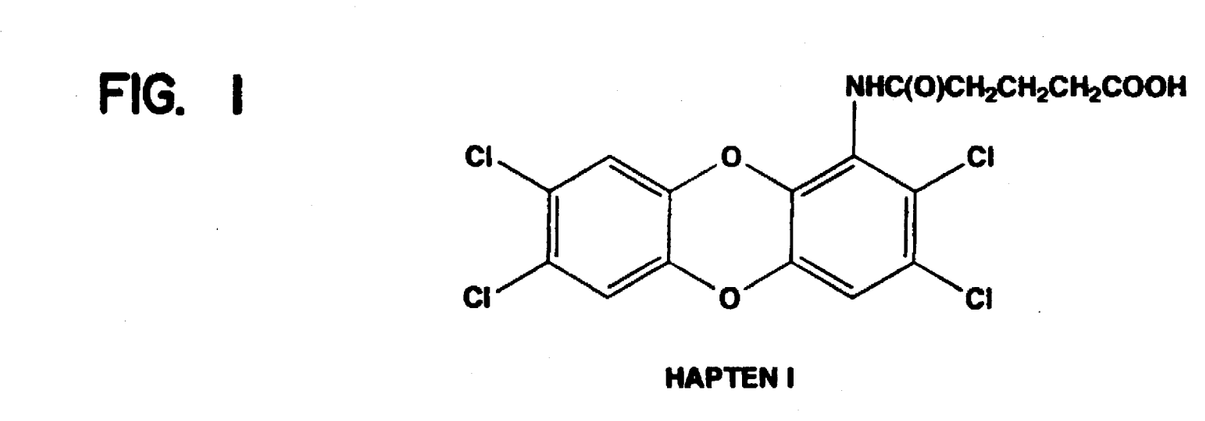
FIG. 1 presents the structure of Hapten I.
Figure 2A:
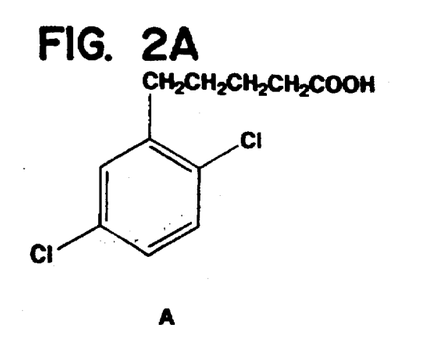
FIG. 2 presents structures of Competitors A-F.
Figure 2B:
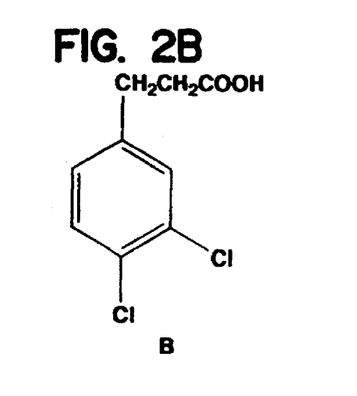
Figure 2C:
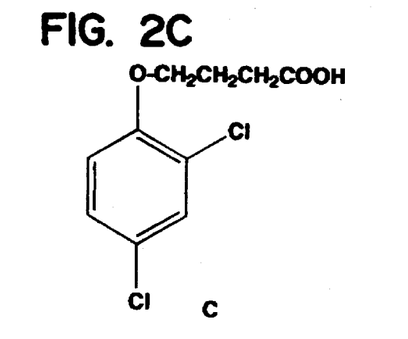
Figure 2D:
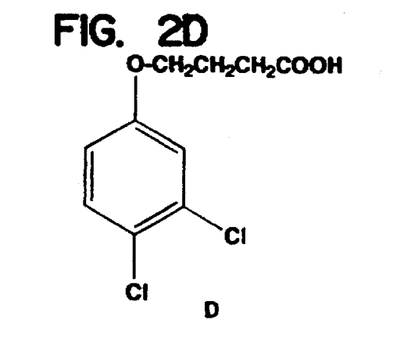
Figure 2E:
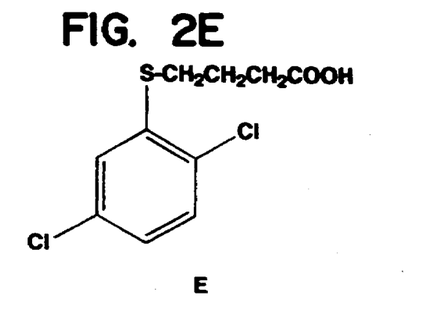
Figure 2F:
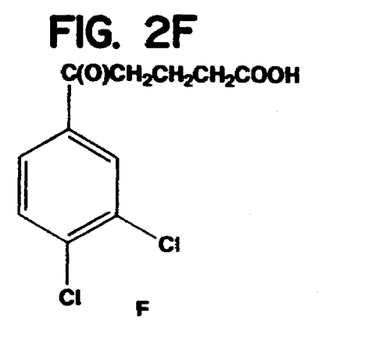

Antibodies can be readily prepared by standard methods. The monoclonal antibody (DD-3) used to demonstrate this invention was obtained from the American Type Culture Collection (ATCC Accession No. HB 9742). M. Vanderlaan, et al., U.S. Pat. No. 4,798,807 (1989). The structure of the hapten which was used to prepare this antibody is given in FIG. 1.

Enzyme Immunoassay

The direct enzyme immunoassay was readily performed using a combination of commercial materials, known formats and the antibody and competitor conjugate materials described in this invention.

Example 1

Synthesis of Exemplified Haptens—ETHER LINK

Exemplified Haptens I, II and III can be prepared from suitably substituted polychlorophenol and polychloroanisole synthons to give polychlorodibenzo-p-dioxin derivatives with a free phenol moiety. G. Mason and S. Safe, *Toxicology*, 41, 153–159 (1986). The phenol can subsequently be utilized in the preparation of the linker derivative via alkylation with a bromoalkylcarboxylate derivative. Exemplified Hapten X can be prepared from a free phenol derivative of dibenzofuran which has been prepared by ring closure of a suitably substituted o-hydroxybiphenyl. T. Humppi, *Chemosphere*, 15, 2003–2006 (1986).

EXAMPLE 2

Synthesis of Exemplified Haptens—ALKYL LINK

Exemplified Hapten VI can be prepared from suitably substituted polychlorophenol and polychlorotoluene derivatives via a polychloromethyldibenzo-p-dioxin intermediate. M. A. Denomme, et al., *Mol. Pharmacol.*, 27., 656–661 (1985). The linker derivative can subsequently be prepared from the methyl anion and a protected bromoalkylcarboxylate moiety. Exemplified Hapten XV can be prepared similarly via a polychloromethyl-o-hydroxybiphenyl intermediate. T. Humppi, *Chemosphere*, 15, 2003–2006 (1986).

EXAMPLE 3

Synthesis of Exemplified Hapten—AMINE and AMIDE LINK

Exemplified Hapten VII can be prepared via nitration of a suitably substituted polychlorodibenzo-p-dioxin or by synthesis of the polychloronitrodibenzo-p-dioxin intermediate from suitable polychlorophenol and polychloronitrophenol starting materials followed by isolation of the desired isomer and reduction to form the amino derivative. K. Chae, et al., *J. Aqric. Food Chem.*, 25, 1207–1209 (1977). The amine can be alkylated in a stepwise sequence to produce an amine or ammonium linker or acylated to prepare the amide linker. Exemplified Hapten XIV can be prepared in an analogous manner. A. Norstrom, et al., *Chemosphere*, 80, 331–343 (1979).

EXAMPLE 4

Synthesis of Exemplified Hapten—THIOETHER LINK

Exemplified Haptens IV, V and XI can be prepared in an analogous sequence to the ether haptens using a suitable chlorothioanisole precursor.

EXAMPLE 5

Synthesis of Exemplified Hapten—CARBONYL LINK

Exemplified Haptens VIII and XII can be prepared by the Friedel-Crafts acylation of the appropriate polychlorodibenzo-p-dioxin or dibenzofuran followed by isolation of the desired isomer.

EXAMPLE 6

Synthesis of Exemplified Hapten—ALKENE LINK

Exemplified Haptens IX and XIII can be prepared by reductive dehydration of suitable carbonyl link haptens.

EXAMPLE 7

Hapten Conjugation Procedure

Hapten can be conjugated to the carrier proteins keyhole limpet hemocyanin and bovine serum albumin through a carbodiimide mediated carboxyl activation procedure. Control reactions which contained hapten and protein without the activating agent can be used to evaluate the efficiency of the aqueous isopropanol dialysis procedure for removal of unreacted, unbound or non-covalent hapten from the conjugate solution. Hapten loads are assessed using a differential UV/Vis procedure.

Hapten Conjugation

Hapten, calculated to be a 200 fold molar excess over keyhole limpet hemocyanin (KLH) or a 100 fold molar excess over bovine serum albumin (BSA) is dissolved in 400 μl dimethylformamide (Aldrich, gold label) and preactivated to form the n-hydroxysuccinimide (NHS) ester. The activation is carried out using a 1.4 fold molar excess (calculated over the hapten) of 1-ethyl-3-[3-dimethylaminopropyl]-carbodiimide (EDC) and a 2 fold molar excess (calculated over the hapten) of NHS added dry to the hapten solution.

The carrier protein is dissolved in borate buffer (0.1M, pH 9.4) to a final concentration of 10 mg/ml. The protein solution is allowed to stir overnight at 0°–5° C. to ensure that all of the protein is dissolved. Dimethylformamide (Aldrich, gold label) is added to a concentration of 5% (v/v). The preactivated hapten solution is added to the protein solution, 10 μl at a time, every 30–60 minutes, using a 10 μl pipettor. The conjugation mixtures are allowed to stir overnight at room temperature after the hapten solution had been added.

The reaction solutions are transferred to wetted cellulose dialysis tubing (mw cutoff 12,000–14,000) and dialyzed versus 0.5–1.0 L volumes of 10% (v/v) isopropanol in phosphate buffered saline (PBS, pH 7.4) for two days, changing to fresh dialysate buffer after the first day. Controls containing no EDC have shown that this method is successful in removing any nonspecifically bound hapten from the carrier protein.

The reaction solutions are then dialyzed versus 0.5–1.0 L volumes of PBS for 2 days to remove any traces of isopropanol, changing to fresh PBS after the first day. After dialysis, the conjugate solutions are collected from the dialysis tubing.

Load Determination

The moles of carrier protein are determined by the Lowry method with the use of an appropriate standard curve. O. H. Lowry, et al., *J. Biol. Chem.*, 193, 265–275 (1954). The moles of hapten are determined using UV/Vis analysis of the conjugate and the UV/Vis spectrum of the hapten. The conjugate load is determined by dividing the moles of hapten present by the moles of carrier protein (KLH, 300,000 daltons; BSA, 67,000 daltons).

EXAMPLE 8

Synthesis of Competitors

Competitors A–F (FIG. 2) are readily available from commercial sources or prepared via known syntheses.

| Competitor | Source |
| --- | --- |
| A | Described in Example 9 |
| B | Commercial Product, Aldrich Chemical Co. |
| C | Commercial Product, Aldrich Chemical Co. |
| D | Known Synthesis, V. Tandon et al., Indian J. Chem., Sect. B., 15B, 264–266 (1977) |
| E | Known Synthesis, S. Kukalenko, Zh. Org. Khim., 6, 680–684 (1970) |
| F | Known Synthesis, A. Rosowsky, et al., J. Hetero. Chem., 8, 789–793 (1971) |

EXAMPLE 9

Synthesis of Competitor A

The anion of 2,5-dichlorotoluene was reacted with trimethyl 4-bromoorthobutyrate to produce methyl 5-(2,5-dichlorophenyl)pentanoate after mild hydrolytic work-up. Competitor A was prepared by LiOH hydrolysis of the methyl ester.

Methyl 5-(2,5-dichlorophenyl)pentanoate

Diisopropylamine (841 μl, 6 mmol) was added to 20 ml of tetrahydrofuran under nitrogen atmosphere and cooled to 0° C. 5.5 ml of 2.5N n-butyllithium (13 mmol) was added and the reaction was stirred for 20 minutes. The reaction was then cooled to −78° C. 2,5-Dichlorotoluene (642 ul, 5 mmol) was added and stirring was continued for 2 hours at −78° C. Trimethyl 4-bromoorthobutyrate (1.14 g, 5 mmol) was added to the reaction mixture in 10 ml tetrahydrofuran. The reaction was stirred for 5 minutes at −78° C., allowed to come to room temperature and stirred overnight. The reaction was worked-up by adding 10 ml of saturated $KH_2PO_4$, removal of most of the tetrahydrofuran on a rotary evaporator followed by partitioning of the aqueous residue between ethyl acetate and 1N HCl. The organic phase was washed twice with 1N HCl, once with 5% sodium bicarbonate, dried over anhydrous sodium sulfate and concentrated to a residue. Flash chromatography (silica gel; hexane/toluene (39/1)) of the residue gave 1.10 g (84%; GC retention time=15.8 minutes) of a water white oil. 1H NMR (300 MHz, $CDCl_3$) delta=7.24 (d, J=8.5 Hz, H3), 7.18 (d, J=2.5 Hz, H6), 7.09 (dd, J=2.5, 8.5 Hz, H4), 3.66 (s, —COO$CH_3$), 2.69 (t, J=7.8 Hz, Ar—$CH_2$—), 2.35 (t, J=7.0 Hz, —$CH_2$—COO—), 1.70–1.55 (m, —$CH_2$—$CH$—C$H_2$—$CH_2$—).

5-(2,5-dichlorophenyl)pentanoic acid. (Competitor A)

Methyl 5-(2,5-dichlorophenyl)pentanoate (1.10 g, 4.2 mmol) was dissolved in 20 ml tetrahydrofuran and 7 ml methanol. 1N LiOH (12 ml) was added dropwise and the reaction was stirred at room temperature for 2 days. The reaction was worked-up by acidification with 2N HCl and removal of most of the tetrahydrofuran and methanol on a rotary evaporator followed by extraction of the aqueous residue with ethyl acetate. The organic phase was washed with water and saturated brine, dried over anhydrous sodium sulfate and concentrated to a residue. Flash chromatography (silica gel; hexane/toluene (19/1) with 1% acetic acid) of the residue gave 725 mg (70%) of a white solid. $^1$H NMR (200 MHz, $CD_3OD$) delta=7.30–7.26 (m, H3, H6), 7.14 (dd, J=2.6, 8.4 Hz, H4), 2.70 (t, J=7.2 Hz, Ar-$CH_2$—), 2.30 (t, J=7.0 Hz, —$CH_2$—COOH), 1.67–1.57 (m, —$CH_2$—C$H_2$—$CH_2$—); MS (EI, m/z (relative intensity)) 248 (29), 246 ($M^+$, 45), 167 (31), 165 (97), 161 (66), 159 (100); exact mass calculated for $C_{11}H_{12}Cl_2O_2$, $[M]^+$ 246.0213, found 246.0210.

EXAMPLE 10

Synthesis of Exemplified Competitors—THIOETHER LINK

Exemplified Competitors 1, 7 and 10 can be prepared by alkylation of the appropriate chlorothiophenol with an alkyl

19 bromide linker. Exemplified Competitor 14 can be prepared via a polychlorothiphenol through dioxane ring closure from an o-phenol intermediate or by direct thio linker substitution on a polychlorobenzodioxin. L. Testaferri, et al., *Tetrahedron Lett.*, 21, 3099–3100 (1980).

EXAMPLE 11

Synthesis of Exemplified Competitors—ETHER LINK

Exemplified Competitors 2, 6, 11 and 12 can be prepared by alkylation of the appropriate chlorophenol with an alkyl bromide linker. Exemplified Competitor 17 can be prepared similarly to the ether link hapten (Example 1).

EXAMPLE 12

Synthesis of Exemplified Competitors—ALKYL LINK

Exemplified Competitors 3, 4 and 5 can be prepared from the chlorotoluene by a methyl anion and protected bromoalkylcarboxylate moiety based reaction. Exemplified Competitors 13 and 16 can be prepared from a suitable polychlorophenol intermediate. Exemplified Competitor 20 can be prepared similarly to the alkyl link hapten (Example 2).

EXAMPLE 13

Synthesis of Exemplified Competitors— CARBONYL LINK

Exemplified Competitor 8 can be prepared by Friedel-Crafts acylation of the appropriate chlorobenzene followed by isolation of the desired isomer. Exemplified Competitor 15 can be prepared in a similar fashion from a suitable polychlorobenzofuran. Exemplified Competitor 18 can be prepared similarly to the carbonyl link hapten (Example 5).

EXAMPLE 14

Synthesis of Exemplified Competitors—ALKENE LINK

Exemplified Competitor 9 can be prepared by reductive dehydration of a suitable carbonyl link derivative. Exemplified Competitor 19 can be prepared similarly to the alkene link hapten (Example 6).

EXAMPLE 15

Synthesis of Hapten I and Competitor Enzyme Conjugates

The competitors A–F (FIG. 2) and Hapten I (FIG. 1) were conjugated to the enzyme, amino modified Horseradish Peroxidase (HRP) (horseradish peroxidase commercially available from Sigma Chemical Co. (No. P-6782), St. Louis, Mo.; amino modified per R. Hsiao and H. Royer, Archives Biochem. Biophys., 198, 379–385 (1979) to give 6–24 free amines), using the carbodiimide mediated carboxyl activation procedure described in Example 7. Hapten and competitor load were determined by UV/Vis spectroscopy, also as described in Example 7.

EXAMPLE 16

Method A: Direct EIA

The direct EIA (immobilized antibody and competitor enzyme conjugate) was performed as follows. Monoclonal antibody supernatant stored at −20° C. was diluted 1,000–40,000 fold with PBS which contained 0.1% Tween-20. This solution was dispensed (500 ul) into donkey anti-mouse second antibody coated tubes (DAM Tubes commercially available from Millipore Corp., Bedford, Mass.) and incubated at room temperature overnight. The antisera solution was decanted from the tubes and the tubes washed 3 times with distilled water. Non-specific sites in the tubes were blocked with 600 ul of BSA blocking buffer (EIA Blocking Buffer commercially available from Millipore Corp., Bedford, Mass.) and incubated for 2 hours at room temperature or overnight at 4° C. The blocking buffer was decanted and the tubes allowed to dry under ambient room conditions for at least 2 hours. The assay was performed by adding 500 ul of assay diluent (1% methanol (v/v) and 0.005% Tween-20 (w/v) in distilled water) to the required number of tubes followed by 10 ul of a methanol solution of the analyte (PCDD or PCDF). After a 5 minute incubation at room temperature, the solution was decanted and the tubes rinsed 3–4 times with tap water. The horseradish peroxidase competitor or Hapten I conjugates were diluted 1,000–60,000 fold from 2–5 mg/ml stock solutions in PBS with conjugate diluent (Enzyme Conjugate Diluent commercially available from Millipore Corp., Bedford, Mass.). The enzyme conjugate (200 ul) was added to the tubes followed by a 5 minute incubation at room temperature. The conjugate solution was decanted and the tubes rinsed 3–4 times with tap water. Enzyme substrate solution (500 ul, KPL No. 50-76-04 commercially available from KPL Laboratories, Gaithersburg, Md.) was added and the tubes were incubated at room temperature for 5–15 minutes. The enzyme reaction was stopped with the addition of 500 ul of 1N HCl. The OD of the solution was determined at 450 nm. The data was plotted using Log (Congener Concentration) versus B/Bo (B=Sample Absorbance, Bo=Sample Blank Absorbance).

EXAMPLE 17

Demonstration of a High Sensitivity Direct EIA Based on a Competitor Conjugate

Figure 3:
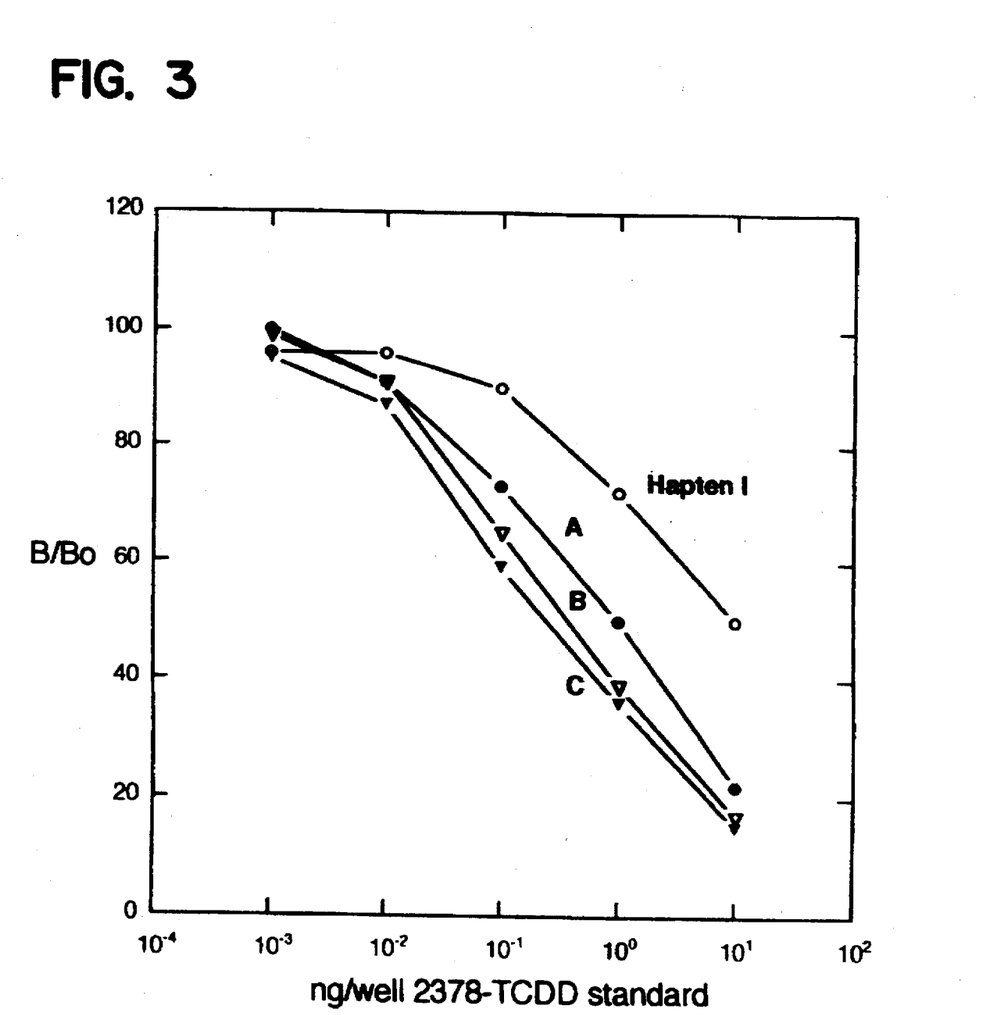
FIG. 3 shows results of a direct format EIA using as competitors Hapten I and Competitors A-C with 2,3,7,8-tetrachlorodibenzo-p-dioxin as the analyte.

The direct EIA (Method 16) was used to evaluate various competitors (FIG. 2) versus the DD-3 antibody. FIG. 3 and Table I demonstrate that Competitors A, B, C, D, E and F produce assays which are significantly more sensitive than the Hapten I enzyme conjugate based assay.

TABLE I

Comparison of Competitor Derived 2,3,7,8-Tetrachlorodibenzo-p-dioxin EIA Sensitivities Using the DD-3 Antibody

| COMPETITOR | $I_{85}$ (mdl, pg/well) | $I_{50}$ (pg/well) |
|---|---|---|
| Hapten I | 200 | 10,000 |
| Competitor A | 25 | 1,000 |
| Competitor B | 20 | 350 |
| Competitor C | 13 | 230 |
| Competitor D | 15 | 380 |
| Competitor E | 15 | 380 |
| Competitor F | 13 | 230 |

EXAMPLE 18

Demonstration of Assay Specificity

The specificity of the DD-3 antibody for toxic congeners of PCDD and PCDF has been defined using the Hapten I based assay and mixtures of various PCDDs and PCDFs as analytes. L. H. Stanker, et al., *Toxicology*, 45, 229–243

Figure 4:
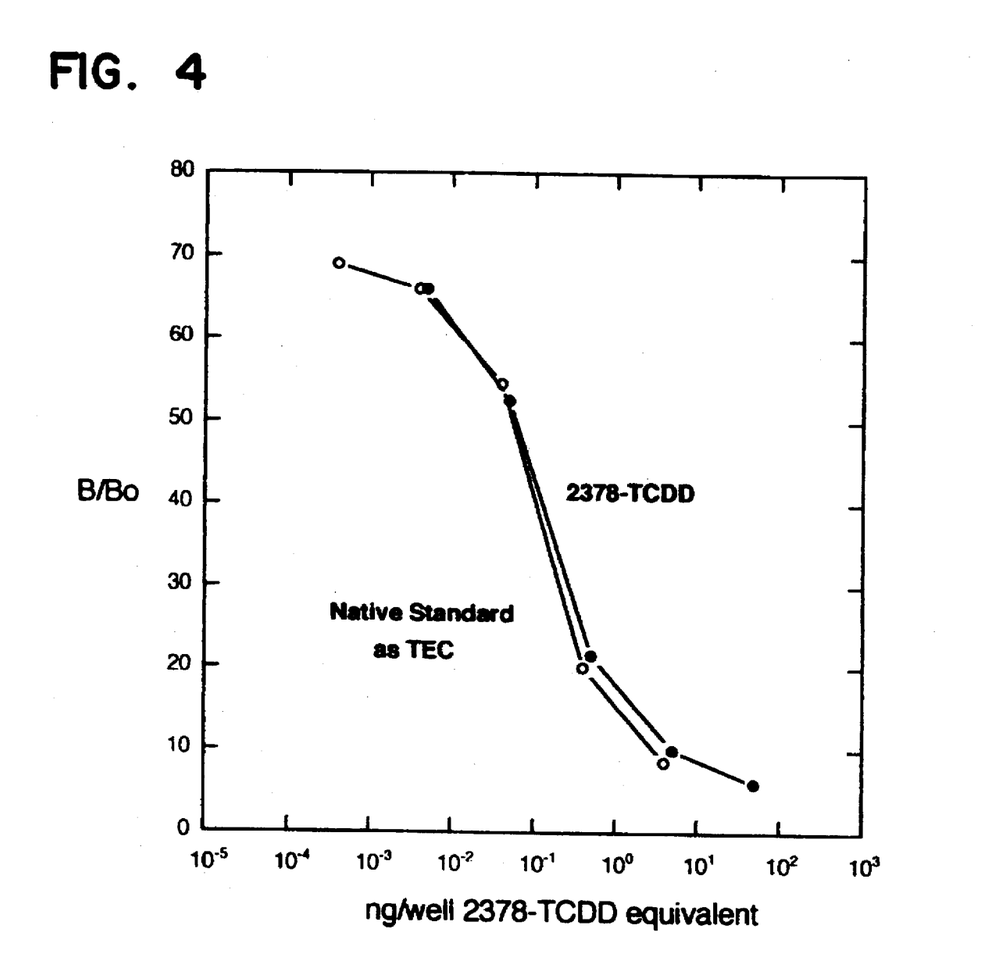
FIG. 4 shows results of a direct format EIA using competitor F with a TEF mixture of PCDD and PCDF toxic congeners as the analyte.

(1987). The recognition profile of this antibody corresponds to the Toxicity Equivalence Factors (TEFs) which have been determined for these congeners. F. W. Kutz, et al., Chemosphere, 20., 751–757 (1990). Competitive inhibition direct EIAs using a standard mixture of toxic congeners of PCDD and PCDF, the TEF Mixture (Table II), and Competitors B and C was performed to evaluate the specificity of the competitor based assays. The close match of the 2,3,7,8-tetrachlorodibenzo-p-dioxin and the TEF Mixture standard curves (FIG. 4) demonstrates the specificity of the assay.

TABLE II

Composition of Native Standard and Toxic Equivalent Concentrations

| Congener | pg/μl Used | TEF* | TEC** |
|---|---|---|---|
| 2,3,7,8-TCDF | 4 | 0.1 | 0.4 |
| 2,3,7,8-TCDD | 4 | 1 | 4 |
| 1,2,3,7,8-PeCDF | 20 | 0.05 | 1 |
| 2,3,4,7,8-PeCDF | 20 | 0.5 | 10 |
| 1,2,3,7,8-PeCDD | 20 | 0.5 | 10 |
| 1,2,3,4,7,8-HxCDF | 20 | 0.1 | 2 |
| 1,2,3,6,7,8-HxCDF | 20 | 0.1 | 2 |
| 2,3,4,6,7,8-HxCDF | 20 | 0.1 | 2 |
| 1,2,3,7,8,9-HxCDF | 20 | 0.1 | 2 |
| 1,2,3,4,7,8-HxCDD | 20 | 0.1 | 2 |
| 1,2,3,6,7,8-HxCDD | 20 | 0.1 | 2 |
| 1,2,3,7,8,9-HxCDD | 20 | 0.1 | 2 |
| 1,2,3,4,6,7,8-HpCDF | 20 | 0.01 | 0.2 |
| 1,2,3,4,7,8,9-HpCDF | 20 | 0.01 | 0.2 |
| 1,2,3,4,6,7,9-HpCDD | 20 | 0.01 | 0.2 |
| OCDF | 40 | 0.001 | 0.04 |
| OCDD | 40 | 0.001 | 0.04 |
| Total | 348 | | 40.08 |

*TEF = toxic equivalency factor
**TEC = toxic equivalency concentration (pg/μl used × TEF = TEC)

EXAMPLE 19

Demonstration of 2,3,7,8-Tetrachlorodibenzofuran Sensitivity

Evaluation of assay sensitivity to 2,3,7,8-tetrachlorodibenzofuran using the direct competition EIA with DD-3 and Competitor F gave a standard curve with an $I_{85}$ (mdl) of 80 pg/well and an $I_{50}$ of 800 pg/well. This result, which is about a factor of 10 more sensitive than is observed with the DD-3 and Hapten I assay system (L. H. Stanker, et al., Toxicology, 45, 229–243 (1987)), demonstrates that these competitors can be used in the development of a sensitive PCDF assay.

We claim:

1. A method for determining qualitatively or quantitatively the presence of polychloro dibenzodioxin or polychloro dibenzofuran in a test sample comprising the steps of:

(a) providing a known quantity of antibody to polychloro dibenzodioxin or polychloro dibenzofuran;

(b) providing a detectable competitor that will bind to said antibody in competition with polychloro dibenzodioxin or polychloro dibenzofuran; wherein said competitor has one of the following structures:

FORMULA I  FORMULA II

FORMULA III  FORMULA V

FORMULA VI wherein (i) A is a single bond or an organic or inorganic linking group capable of forming covalent bonds with a phenyl ring and with B simultaneously;

(ii) B is a single bond or an organic or inorganic linking group capable of forming covalent bonds with A and C simultaneously;

(iii) C is a single bond or an organic or inorganic linking group capable of forming simultaneous covalent bonds with B and a conjugate moiety;

(iv) D is a single bond or an organic or inorganic linking group capable of forming covalent bonds with an alkyl ring and with E;

(v) E is a single bond or an organic or inorganic linking group capable of forming covalent bonds with D and F simultaneously;

(vi) F is a single bond or an organic or inorganic linking group capable of simultaneously forming covalent bonds with E and a conjugate, moiety;

(vii) l=0–5;

(viii) m=0–4;

(ix) n=0–3;

(c) incubating said antibody and said competitor in the presence of a test sample; and (d) detecting the presence of the competitor;

(e) correlating the competitor detected with the presence or quantity of polychloro dibenzodioxin or polychloro dibenzofuran in the test sample.

2. The method of claim 1, wherein A is selected from the group consisting of —NH—, —S—, —O—, —CH$_2$—, —C(O)—, —CH=CH—, —NH—C(O)—, —C(O)—NH—, —NH—C(O)—NH—, —NH—C(S)—NH—, —N(CH$_3$)—, —N(CH$_3$)$_2$—, and —OC(S)NH—.

3. The method of claim 1, wherein A is selected from the group consisting of —O—, —S—, —CH$_2$—, —C(O)— and —CH=CH—.

4. The method of claim 1, wherein B is a C$_1$-C$_{10}$ alkyl including —S—, —NH—, or 1-4 nonperoxide —O—.

5. The method of claim 1, wherein C is selected from the group consisting of —CO$_2$H, —NH$_2$, —CHO, and —OH.

6. The method of claim 1 wherein D is selected from the group consisting of —CH₂—, and —CH=CH—.

7. The method of claim 1, wherein E is a $C_1$–$C_{13}$ alkyl including —S—, —NH—, or 1–4 nonperoxide —O—.

8. The method of claim 1, wherein F is selected from the group consisting of —CO₂H, —NH₂, —CHO, and —OH.

9. The method of claim 1, wherein the competitor has the general structure of Formula I.

10. The method of claim 1, wherein the competitor has the general structure of Formula II, Formula III, Formula V, or Formula VI.

11. The method of claim 1, wherein the competitor is bound to a solid support.

12. The method of claim 1, wherein the competitor is bound to a protein.

13. The method of claim 1, wherein the step of detecting comprises the use of an enzymatic label.

14. The method of claim 13, wherein the step of detecting is an EIA determination.

15. The method of claim 1, wherein the polychloro dibenzodioxin or polychloro dibenzofuran is a toxic congener of PCDD or PCDF.

16. The method of claim 15, wherein the polychloro dibenzodioxin or polychloro dibenzofuran is selected from the group consisting of 2,3,7,8-tetrachloro dibenzo-p-dioxin, 1,2,3,7,8-pentachloro dibenzo-p-dioxin, 1,2,3,4,7,8-hexachloro dibenzo-p-dioxin, 1,2,3,6,7,8-hexachloro dibenzo-p-dioxin, 1,2,3,7,8,9-hexachloro dibenzo-p-dioxin, 1,2,3,4,6,7,8-heptachloro dibenzo-p-dioxin, 1,2,3,4,6,7,9-heptachloro dibenzo-p-dioxin, octachloro dibenzo-p-dioxin, 2,3,7,8-tetrachloro dibenzofuran, 1,2,3,7,8-pentachloro dibenzofuran, 2,3,4,7,8-pentachloro dibenzofuran, 1,2,3,4,7,8-hexachloro dibenzofuran, 1,2,3,6,7,8-hexachloro dibenzofuran, 1,2,3,7,8,9-hexachloro dibenzofuran, 2,3,4,6,7,8-hexachloro dibenzofuran, 1,2,3,4,6,7,8-heptachloro dibenzofuran, 1,2,3,4,7,8,9-heptachloro dibenzofuran, octachloro dibenzofuran, and combinations thereof.

17. The method of claim 1, wherein said antibodies are prepared by inoculating a host animal with a hapten-protein complex, wherein the hapten has the following structure, and collecting the serum or preparing monoclonal antibodies from the host animal:

FORMULA VIII

FORMULA IX wherein
(i) L is a single bond or an organic or inorganic linking group capable of forming covalent bonds with a phenyl ring and with M;
(ii) M is a single bond or an organic or inorganic linking group capable of forming covalent bonds with L and N simultaneously;
(iii) N is a single bond or an organic or inorganic linking group capable of forming simultaneous covalent bonds with M and a conjugate moiety;

(iv) m=0–4; and
(v) n–0–3.

18. The method of claim 17, wherein L is selected from the group consisting of —NH—, —S—, —O—, —CH₂—, —C(O)—, —CH=CH—, —NH—C(O)—, —C(O)—NH—, —NH—C(O)—NH—, —NH—C(S)—NH—, —N(CH₃)₂, —N(CH₃)—, and —OC(S)NH—.

19. The method of claim 1, wherein N is selected from the group consisting of —CO₂H, —NH₂, —CHO, and —OH.

20. The method of claim 17 wherein the hapten is covalently bound to a protein.

21. The method of claim 17, further comprising preparing affinity purified antibody fractions using hapten bound to a solid support.

22. A method for determining qualitatively or quantitatively the presence of substituted polychloro dibenzodioxin or substituted polychloro dibenzofuran comprising the steps of:

(a) providing a known quantity of antibody to the analyte;
(b) providing a detectable competitor that will bind to said antibody in competition with the analyte; wherein said competitor has one of the following structures:

FORMULA I wherein
(i) A is a single bond or an organic or inorganic linking group capable of forming covalent bonds with a phenyl ring and with B simultaneously;
(ii) B is a single bond or an organic or inorganic linking group capable of forming covalent bonds with A and C simultaneously;
(iii) C is a single bond or an organic or inorganic linking group capable of forming simultaneous covalent bonds with B and a conjugate moiety;
(iv) l=0–5;

(c) incubating said antibody and said competitor in the presence of a test sample including the analyte; and
(d) detecting the presence of the competitor;
(e) correlating the competitor detected with the presence or quantity of substituted polychloro dibenzodioxin or substituted polychloro dibenzofuran in the test sample.

23. A method for determining qualitatively or quantitatively the presence of polychloro dibenzodioxin or polychloro dibenzofuran in a test sample comprising the steps of:

(a) providing a known quantity of antibody to polychloro dibenzodioxin or polychloro dibenzofuran;
(b) providing a detectable competitor that will bind to said antibody in competition with polychloro dibenzodioxin or polychloro dibenzofuran; wherein said competitor has one of the following structures:

FORMULA IV

FORMULA VII wherein
(i) A is selected from the group consisting of —S—, —CH$_2$—, —C(O)—, —CH=CH—, —NH—C(S)NH—, —N(CH$_3$)—, —N(CH$_3$)$_2$—, and —OC(S)NH—;

(ii) B is a C$_1$–C$_{10}$ alkyl including —S—, —NH—, or 1–4 nonperoxide —O—;
(iii) C is selected from the group consisting of —CO$_2$H, —NH$_2$, —CHO, and —OH;
(vii) m=0–4;
(viii) n=0–3;

(c) incubating said antibody and said competitor in the presence of a test sample; and
(d) detecting the presence of the competitor;
(e) correlating the competitor detected with the presence or quantity of polychloro dibenzodioxin or polychloro dibenzofuran in the test sample.

* * * * *

UNITED STATES PATENT AND TRADEMARK OFFICE
CERTIFICATE OF CORRECTION

PATENT NO. : 5,674,697

DATED : OCTOBER 7, 1997

INVENTOR(S) : CARLSON

It is certified that error appears in the above-identified patent and that said Letters Patent is hereby corrected as shown below:

Title page, [56] References Cited, Foreign Patent Documents: The last line that reads "A 4/1995 WIPO" should be moved up one line to read --WO 9506249A  4/1995  WIPO.--

Col. 1, line 35: "PCDO" should read --PCDD--

Col. 22, line 15, claim 1, Formula V:

" should read --  --

Col. 23, line 3, claim 7: "$C_1-C_{13}$" should read --$C_1-C_{10}$--

Signed and Sealed this

Fourteenth Day of December, 1999

*Attest:*

Q. TODD DICKINSON

*Attesting Officer*   *Acting Commissioner of Patents and Trademarks*